United States Patent
Pauli et al.

(10) Patent No.: US 9,125,685 B2
(45) Date of Patent: Sep. 8, 2015

(54) TROCAR DEVICE

(71) Applicant: Henke-Sass, Wolf GmbH, Tuttlingen (DE)

(72) Inventors: Sabine Pauli, Seitingen-Oberflacht (DE); Norbert Haeckl, Leibertingen (DE); Michael Fuchs, Seitingen-Oberflacht (DE)

(73) Assignee: Henke-Sass, Wolf GmbH, Tuttlingen (DE)

( * ) Notice: Subject to any disclaimer, the term of this patent is extended or adjusted under 35 U.S.C. 154(b) by 0 days.

(21) Appl. No.: 13/927,084

(22) Filed: Jun. 25, 2013

(65) Prior Publication Data

US 2013/0345637 A1    Dec. 26, 2013

(30) Foreign Application Priority Data

Jun. 26, 2012   (DE) .......................... 10 2012 210 837

(51) Int. Cl.
  *A61B 17/00*   (2006.01)
  *A61B 17/34*   (2006.01)
  *A61M 39/06*   (2006.01)

(52) U.S. Cl.
  CPC .............. *A61B 17/3462* (2013.01); *A61B 17/34* (2013.01); *A61M 2039/0626* (2013.01)

(58) Field of Classification Search
  CPC ............ A61M 39/06; A61M 39/0606; A61M 39/0613; A61M 39/0693; A61M 2039/0626; A61B 17/34; A61B 17/3498; A61B 2017/3464; A61B 17/3462; A61B 2017/347
  USPC .......... 604/513, 164.01, 167.02, 167.06, 264, 604/278, 158, 160; 606/1
  See application file for complete search history.

(56) References Cited

U.S. PATENT DOCUMENTS

| | | | | |
|---|---|---|---|---|
| 3,853,127 A | * | 12/1974 | Spademan | 604/167.01 |
| 4,649,904 A | * | 3/1987 | Krauter et al. | 600/154 |
| 5,779,697 A | * | 7/1998 | Glowa et al. | 606/185 |
| 5,993,471 A | | 11/1999 | Riza et al. | |
| 8,357,123 B2 | | 1/2013 | Gresham | |
| 2004/0199126 A1 | * | 10/2004 | Harding et al. | 604/256 |
| 2009/0234293 A1 | | 9/2009 | Albrecht et al. | |
| 2010/0087705 A1 | * | 4/2010 | Byers et al. | 600/104 |
| 2010/0249710 A1 | | 9/2010 | Blier et al. | |

FOREIGN PATENT DOCUMENTS

| | | |
|---|---|---|
| DE | 102010028049 A1 | 10/2011 |
| EP | 0517248 A1 | 9/1992 |
| EP | 2036508 A1 | 3/2009 |
| EP | 2233089 A1 | 9/2010 |
| WO | 98/50093 | 11/1998 |

* cited by examiner

*Primary Examiner* — Bhisma Mehta
*Assistant Examiner* — Nicholas Meghri
(74) *Attorney, Agent, or Firm* — Skaar Ulbrich Macari, P.A.

(57) ABSTRACT

A trocar device includes a main part that has a first and a second end. A shaft tube is connected to the second end of the main part. A through-opening for receiving an instrument extends from the first end of the main part to the end of the shaft tube that faces away from the main part. A sealing unit is disposed in the main part and has an elastic sealing element having a hollow-cylindrical wall, which divides the through-opening into a first region that runs from the sealing unit as far as the first end of the main body, and into a second region that runs from the sealing unit as far as the end of the shaft tube that faces away from the main part. When the instrument has been properly inserted in the through-opening, the sealing element seals off the two regions from each other.

14 Claims, 1 Drawing Sheet

TROCAR DEVICE

PRIORITY

This application claims priority to German Patent Application No. 102012210837.8, filed on Jun. 26, 2012, which is hereby incorporated herein by reference in its entirety.

FIELD

The present invention relates to a trocar device and surgical method. More particularly, the present invention in certain embodiments relates to a trocar device comprising: a main part that has a first and a second end; a shaft tube that is connected to the second end of the main part; a through-opening, extending from the first end of the main part as far as the end of the shaft tube that faces away from the main part, for receiving an instrument; and a sealing unit, which is disposed in the main part, and which has an elastic sealing element having a hollow-cylindrical wall comprising a lumen therethrough, the lumen including a continuous inner surface, the sealing element dividing the through-opening into a first region that runs from the sealing unit as far as the first end of the main body, and into a second region that runs from the sealing unit as far as the end of the shaft tube that faces away from the main part, and which, when the instrument has been properly inserted in the through-opening, seals off the two regions from each other.

BACKGROUND

Trocar devices are used for surgical intervention. Typically, the shaft tube of a trocar is disposed at least partially inside the person or animal undergoing the operation, and the main part of the trocar is disposed on the outside. Via this access, appropriate instruments can then be guided through the through-opening in the trocar, thereby enabling the desired surgical intervention to be performed. In particular, an endoscope can be introduced through the through-opening.

In the case of such a use of the trocar device, fluids from the second region (for example, flushing fluids or other bodily fluids) are to be prevented from passing into the first region, and from damaging the instrument (e.g. the endoscope). A sealing unit is therefore provided. Previously, this sealing unit has been realized as a hollow-cylindrical seal, which is glued into the main part. However, it is not thereby possible to achieve permanent fixing of the seal, which then results in unwanted leakages.

SUMMARY

It is therefore the object of certain embodiments of the invention to provide an improved trocar device and system that addresses the above-noted difficulties and eliminates them as completely as possible.

According to one embodiment of the invention, the object is achieved, in the case of a trocar device of the type stated at the outset, in that the sealing unit comprises a holder, which is fastened in the main part and which clamps-in a portion of the hollow-cylindrical wall of the sealing element, such that the sealing element is fixed in the holder. As a result of this clamped mounting of the sealing element, the sealing element is fixed securely and permanently in the holder. The holder, for its part, is securely and permanently fastened in the main part, such that, overall, a permanent seal exists between the two regions of the through-opening.

The sealing unit can be easily produced, since the sealing element is clamped-in only in the main part. Consequently, fixing the sealing element in the holder does not require the sealing element to have notches, which, on the one hand, would necessitate resource-intensive production and, on the other hand, would weaken the sealing element itself. Fixing of the sealing element is achieved by clamping-in, or compressing, the corresponding wall portion in the holder.

The trocar device according to certain embodiments of the invention can also be referred to as a guide device for an endoscope, and can be used both in medical and in non-medical fields.

The holder can include a first holding element, which bears against the continuous inner surface of the lumen of the of the hollow-cylindrical wall such that a clamping force in an outward radial direction is generated. Furthermore, the holder can have a second holding element, which bears against an outer circumferential surface of the hollow-cylindrical wall. The desired clamping-in can thereby be realized in a simple manner. In particular, the first holding element can have a first clamping portion, which projects radially outwards for the purpose of clamping-in the wall portion. It can also be said that the outer diameter of the clamping portion is greater than the inner diameter of the inside of the wall.

Further, additionally or alternatively, the second holding element can include a second clamping portion, which projects radially inwards for the purpose of clamping-in the wall portion. The second clamping portion thus has an inner diameter that is less than the outer diameter of the hollow-cylindrical wall.

For the purpose of fastening the holder in the main part, the holder can have an external thread. In this case, it is screwed into a corresponding internal thread in the main part. The external thread can be realized, for example, on the second holding element.

The holder can be glued to the sealing element. Further, the holder can be glued into the main part.

The sealing element can project over the holder in an axial direction to define a projecting part, wherein the projecting part of the sealing element faces towards the first end. The trocar device can be realized such that, when the instrument (e.g. an endoscope) has been properly inserted in the through-opening, the sealing element is compressed in the axial direction, such that a restoring force, directed towards the first end of the main part, acts upon the instrument.

Further, the trocar device can have a fixing unit, which, when the instrument has been properly inserted in the trocar device, locks the instrument so as to prevent it from moving towards the first end of the main part. For this purpose, the fixing unit can have a slide, which can be moved transversely in relation to the longitudinal direction of the shaft tube and, in a first position, effects the desired locking. The slide can be held in the first position by a spring.

When the slide is moved from a first position to a second position, it no longer effects locking of the instrument, such that the latter can be removed from the trocar device. If, when the instrument is in the proper position, the sealing element acts upon the instrument with a force towards the first end of the main body, the instrument is then as a result moved towards the first end of the main part. This facilitates removal of the instrument from the trocar device.

The sealing element may be made of an elastomer (for example, silicone).

The main part, the shaft tube and/or the holder may be made of metal and/or plastic.

The clamped-in portion of the continuous inner surface of the lumen can be, in particular, a portion extending in the longitudinal direction of the hollow-cylindrical wall. Therefore, only a part of the hollow-cylindrical wall (as viewed in the longitudinal direction) is clamped-in by means of the holder.

In particular, the elastic sealing element can be realized as a hollow cylinder, which comprises the hollow-cylindrical wall. A hollow cylinder is understood here to mean, in particular, that the inner cross section and/or the wall cross section of the hollow cylinder remains constant in the longitudinal direction of the hollow-cylindrical wall. The elastic sealing element can be exclusively in the form of a hollow cylinder.

The extent of the elastic sealing element in the longitudinal direction of the hollow-cylindrical wall in certain embodiments is preferably greater than the inside width of the hollow-cylindrical wall. If the elastic sealing element has, for example, a circular inner cross section, the inside width is the diameter of this inner cross section. Otherwise, this is understood to be, in particular, the maximum extent of the inner cross section.

The hollow-cylindrical wall is preferably of a constant thickness, or wall thickness (disregarding the clamping caused by the holder).

It is understood that the features mentioned above and those yet to be explained in the following are applicable, not only in the stated combination, but also in other combinations or singly, without departure from the scope of the present invention.

BRIEF DESCRIPTION OF THE DRAWINGS

The invention is explained in further detail below by way of example with reference to the attached drawings which also disclose features essential to the invention.

DETAILED DESCRIPTION

The present invention can be explained with reference to the following example embodiments. However, these example embodiments are not intended to limit the present invention to any specific examples, embodiments, environments, applications or implementations described in these embodiments. Therefore, description of these embodiments is only for purpose of illustration rather than to limit the present invention.

Figure 1:
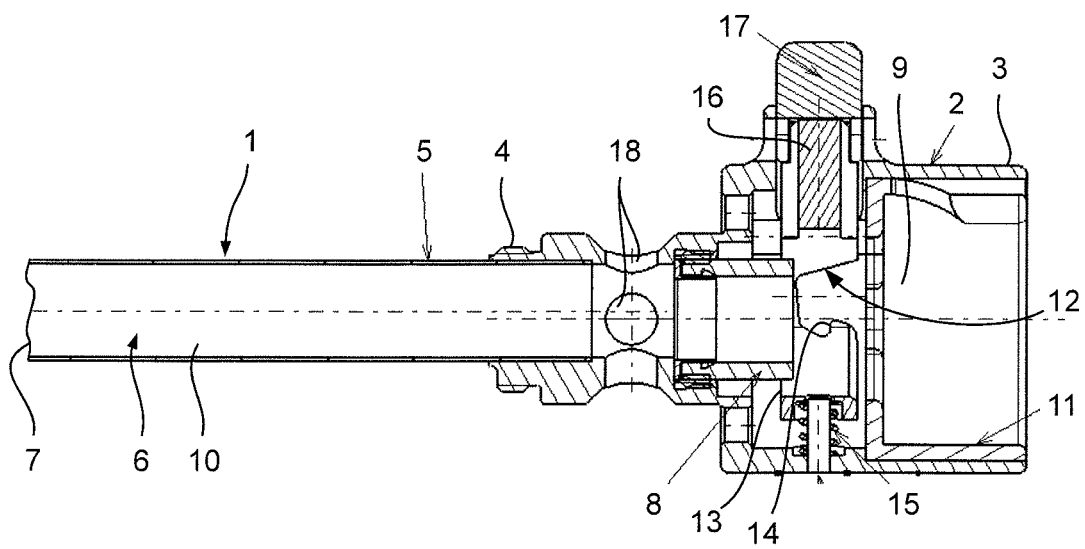
FIG. 1 is a schematic sectional representation of a trocar device according to certain embodiments of the invention.

Referring to FIG. 1, the trocar device 1 comprises a main part 2 that has first and a second end 3, 4, and comprises a shaft tube 5, which is connected to the second end 4 of the main part 2 such that there is a through-opening 6, which extends from the first end 3 of the main part 2 as far as the end 7 (also referred to in the following as the shaft tube end 7) that faces away from the main part 2.

Disposed in the main part 2 is a sealing unit 8, which divides the through-opening into a first region 9, which runs from the sealing unit 8 as far as the first end 3 of the main part 2, and into a second region 10, which runs from the sealing unit 8 as far as the shaft tube end 7.

The trocar device 1 is configured to receive an endoscope (not shown), which is introduced into the through-opening 6 from the first end 3. For this purpose, a guide part 11 is disposed in the region of the first end 3, in the main part 2. In addition, disposed after the guide part 11 there is a fixing unit 12, which has a fixing element 13 that can be moved transversely in relation to the longitudinal direction (from top to bottom in FIG. 1) and that has a shoulder 14. Provided between the fixing unit 12 and the main part 2 there is a spring 15, which presses the fixing unit 12 upwards and holds it in the position shown in FIG. 1. The end 16 of the fixing unit 12 that faces away from the spring 15 is directed out of the main part 2 and provided with a cap 17, such that the fixing unit 12 can be pushed downwards, against the spring force, as a result of the cap 17 being pressed in the direction of the spring 15.

In addition to having the sealing unit 8, the main part 2 has (on the left) openings 18 that open into the second region 10. Via these openings 18, a flushing fluid, for example, can be introduced into the second region 10 of the through-opening 6. When the endoscope (not shown) has been inserted in the through-opening 6, the sealing unit 8 can then serve to seal off the first region 9 from the second region 10, such that no flushing fluid or other fluid can pass out of the second region 10 and into the first region 9 and soil the endoscope.

When the endoscope is inserted in the through-opening 6, it is pushed into the through-opening 6, via the first end 3, in the direction of the shaft tube 5. The endoscope in this case has a recess, which is configured such that, as the endoscope is being pushed in, the region in front of the recess presses against the shoulder 14 and thereby displaces the fixing unit 12 towards the spring 15 and, as the endoscope is introduced further, the fixing unit 12 is moved in the opposite direction because of the spring 15 and, as a result, the shoulder 14 settles into the recess, such that the endoscope is secured against being pulled out of the through-opening 6 (to the right in FIG. 1).

Figure 2:
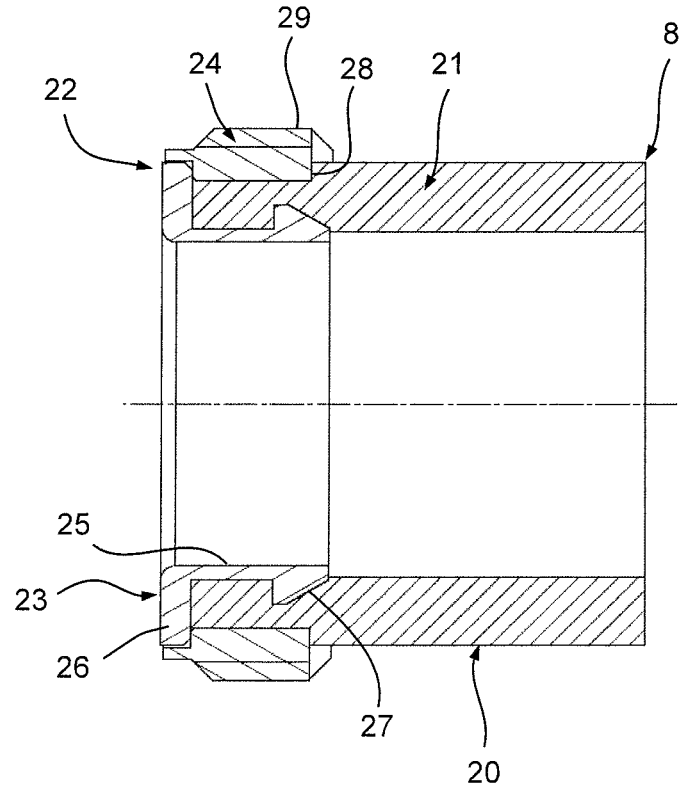
FIG. 2 is an enlarged sectional representation of the sealing unit in the main body according to the embodiment of FIG. 1.

The sealing unit 8 is shown in enlarged form in FIG. 2. It comprises an elastic sealing element 20, which may be made of an elastomer (such as, for example, silicone) and which has a hollow-cylindrical wall 21 defining a lumen therethrough. The continuous inner surface of the lumen is adapted to the endoscope to be introduced. The contour can thus be of a circular, oval, polygonal or other shape. The elastic sealing element 20 is therefore realized as a hollow cylinder. Preferably, the elastic sealing element 20 is exclusively in the form of a hollow cylinder.

Further, the sealing unit 8 comprises a holder 22 having an inner part 23 and an outer part 24. The inner part 23 is realized in the form of a connecting piece and has a hollow-cylindrical region 25 that bears against the inside of the wall 21, and has an annular stop region, which extends radially outwards at the left end of the hollow-cylindrical region 25 and bears against the outside face of the wall. Disposed at the right end of the hollow-cylindrical region 25 there is a shoulder 27, which projects radially outwards and presses the wall 21 outwards.

The outer part 24 is configured as a clamping sleeve that bears against the radial end face of the annular stop region 26 and has a fixing region 28, which adjoins the latter and whose inner diameter is less than the outer diameter of the wall 21. As a result, the portion of the wall located between the inner and the outer part 23, 24 is clamped-in or compressed, such that the sealing element 20 is fixed in the holder 22 as a result.

The outer part 24 additionally has an external thread 29, which is screwed into a corresponding internal thread in the main part 2 (FIG. 1), such that the sealing element 20 is securely fixed in the main part 2 as a result.

As has already been described, the endoscope, when in the inserted state, is fixed in the main part by the fixing unit 12. The trocar device 1 in this case is designed such that the fixed endoscope compresses the sealing element 20 somewhat in the longitudinal direction. The sealing element 20 thus acts upon the endoscope with a force in the direction of the first end 3. If the endoscope is to be removed from the trocar device 1, a user merely has to press the cap 17 in the direction of the spring 15, such that the shoulder 14 is no longer in engagement with the corresponding recess in the endoscope. Owing to the presence of the force applied by the sealing element 20, the endoscope is moved in the direction of the first end 3, such that the user can then easily remove it from the trocar device 1.

The inner and the outer parts may be made of metal (e.g. high-grade steel) and/or also of plastic. The main part may be made of metal (e.g. high-grade steel) and/or of plastic.

The outer part 24 need not have an external thread. It is also possible for the outer part 24 to be glued into the main part.

The above disclosure is related to the detailed technical contents and inventive features thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:

1. A trocar device, comprising:
   a main part having a first end and a second end;
   a shaft tube connected to the second end of the main part;
   a through-opening for receiving an instrument, extending from the first end of the main part to an end of the shaft tube that faces away from the main part;
   a sealing unit disposed in the main part, the sealing unit comprising an elastic sealing element having a hollow-cylindrical wall comprising a lumen therethrough, the lumen including a continuous inner surface, the sealing element dividing the through-opening into a first region that runs from the sealing unit as far as the first end of the main body, and into a second region that runs from the sealing unit as far as the end of the shaft tube that faces away from the main part, and which, when the instrument has been operably inserted in the through-opening, seals off the two regions from each other,
   wherein the sealing unit further comprises a holder fastened in the main part, the holder clamping-in a portion of the hollow-cylindrical wall of the sealing element such that the sealing element is fixed in the holder,
   wherein the holder includes a first holding element, which bears against the continuous inner surface of the lumen of the of the hollow-cylindrical wall such that a clamping force in an outward radial direction is generated, and a second holding element, which bears against an outer circumferential surface of the hollow-cylindrical wall, and
   wherein the sealing element projects over the holder in an axial direction to define a projecting part, wherein the projecting part of the sealing element faces towards the first end.

2. The trocar device according to claim 1, wherein the first holding element includes a first clamping portion, which projects radially outwards to clamp-in the portion of the continuous inner surface of the lumen of the hollow-cylindrical wall.

3. The trocar device according to claim 2, wherein the second holding element includes a second clamping portion, which projects radially inwards to clamp-in the portion of the hollow-cylindrical wall.

4. The trocar device according to claim 1, wherein the second holding element includes a second clamping portion, which projects radially inwards to clamp-in the portion of the hollow-cylindrical wall.

5. The trocar device according to claim 1, wherein the holder includes an external thread, which is screwed into an internal thread in the main part to fasten the holder to the main part.

6. The trocar device according to claim 1, wherein the sealing element comprises an elastomer material.

7. The trocar device according to claim 1, wherein a fixing unit is disposed in the main part, which, when the instrument has been operably inserted in the through opening, locks the instrument so as to prevent it from moving towards the first end.

8. The trocar device according to claim 1, wherein, when the instrument has been operably inserted in the through-opening, the sealing element is compressed in the axial direction, such that a restoring force, directed towards the first end of the main part, acts upon the instrument.

9. The trocar device according to claim 1, wherein the clamped-in portion of the hollow-cylindrical wall extends in a longitudinal direction of the hollow-cylindrical wall.

10. The trocar device according to claim 1, wherein the portion of the hollow-cylindrical wall of the sealing element that is clamped-in by the holder does not extend over an entire extent of the hollow-cylindrical wall in a longitudinal direction of the hollow-cylindrical wall.

11. The trocar device according to claim 1, wherein the sealing element comprises a hollow cylinder.

12. The trocar device according to claim 1, wherein an extent of the sealing element in the longitudinal direction of the hollow-cylindrical wall is greater than an inside width of the hollow-cylindrical wall.

13. The trocar device of claim 1, wherein the hollow cylindrical wall of the sealing element is free from notches.

14. The trocar device of claim 1, wherein the hollow cylindrical wall of the sealing element extends axially beyond the holder toward the first end of the main part.

* * * * *